(12) United States Patent
Proksa (10) Patent No.: US 9,757,081 B2
(45) Date of Patent: Sep. 12, 2017

(54) GRATING-BASED DIFFERENTIAL PHASE CONTRAST IMAGING

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 182 days.

(21) Appl. No.: 14/405,422

(22) PCT Filed: Jun. 20, 2013

(86) PCT No.: PCT/IB2013/055060
§ 371 (c)(1),
(2) Date: Dec. 4, 2014

(87) PCT Pub. No.: WO2014/001975
PCT Pub. Date: Jan. 3, 2014

(65) Prior Publication Data
US 2015/0117598 A1 Apr. 30, 2015

Related U.S. Application Data

(60) Provisional application No. 61/664,950, filed on Jun. 27, 2012.

(51) Int. Cl.
*A61B 6/00* (2006.01)
*A61B 6/03* (2006.01)
*A61B 6/04* (2006.01)

(52) U.S. Cl.
CPC .............. *A61B 6/484* (2013.01); *A61B 6/032* (2013.01); *A61B 6/0457* (2013.01);
(Continued)

(58) Field of Classification Search
CPC ....................................................... A61B 6/484
See application file for complete search history.

(56) References Cited

U.S. PATENT DOCUMENTS 4,052,620 A 10/1977 Brunnett
6,671,345 B2 12/2003 Vrettos et al.
(Continued)

OTHER PUBLICATIONS

Pfeiffer, et al., "Hard X-ray dark-field imaging using a grating interferometer", Nature Materials, vol. 7, No. 2, Feb. 1, 2008.

*Primary Examiner* — Dani Fox (57) ABSTRACT

An imaging system (200) is configured for grating-based DPCI. The imaging system includes a rotating gantry (204) that rotates around an examination region, a radiation source (208), supported by the rotating gantry, that emits radiation that traverses the examination region, a detector array (212), supported by the rotating gantry, that detects radiation that traverses the examination region, and an interferometer, supported by the rotating gantry, which includes a source grating (214), a phase grating (218), and an absorber grating (220). At least one of the phase grating or the absorber grating continuously translates with respect to the other during an integration period and the detector generates and outputs an electrical signal indicative of the detected radiation, wherein the electrical signal includes an absorption component, a coherence component and a phase component.

18 Claims, 5 Drawing Sheets

(52) U.S. Cl.
CPC .......... *A61B 6/4035* (2013.01); *A61B 6/4266* (2013.01); *A61B 6/4291* (2013.01); *A61B 6/4417* (2013.01); *A61B 6/4435* (2013.01); *A61B 6/5205* (2013.01); *A61B 6/54* (2013.01); *A61B 6/035* (2013.01); *A61B 6/502* (2013.01); *A61B 6/504* (2013.01)

(56) References Cited

U.S. PATENT DOCUMENTS

| | | |
|---|---|---|
| 8,139,711 B2 | 3/2012 | Takahashi |
| 8,565,371 B2 | 10/2013 | Bredno |
| 9,269,471 B2 | 2/2016 | Roessl |
| 2009/0092227 A1 | 4/2009 | David et al. |
| 2010/0074395 A1* | 3/2010 | Popescu ............ A61B 6/06 378/16 |
| 2010/0220832 A1 | 9/2010 | Ning et al. |
| 2011/0293064 A1 | 12/2011 | Huang et al. |
| 2012/0243658 A1 | 9/2012 | Geller et al. |

* cited by examiner

GRATING-BASED DIFFERENTIAL PHASE CONTRAST IMAGING

CROSS REFERENCE TO RELATED APPLICATIONS

This application is a national filing of PCT application Ser. No. PCT/IB2013/055060, filed Jun. 20, 2013, published as WO 2014/001975 A2 on Jan. 3, 2014, which claims the benefit of U.S. provisional application Ser. No. 61/664,950 filed Jun. 27, 2012, which is incorporated herein by reference.

The following generally relates to grating-based differential phase contrast imaging (DPCI) and is described with particular application to computed tomography (CT).

In conventional CT imaging, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, in cases where different forms of tissue with similar absorption cross-sections are under investigation (e.g., mammography or angiography), the X-ray absorption contrast is relatively poor. Consequently, differentiating pathologic from non-pathologic tissue in an absorption radiograph obtained with a current hospital-based X-ray system remains difficult for certain tissue compositions.

Figure 1:
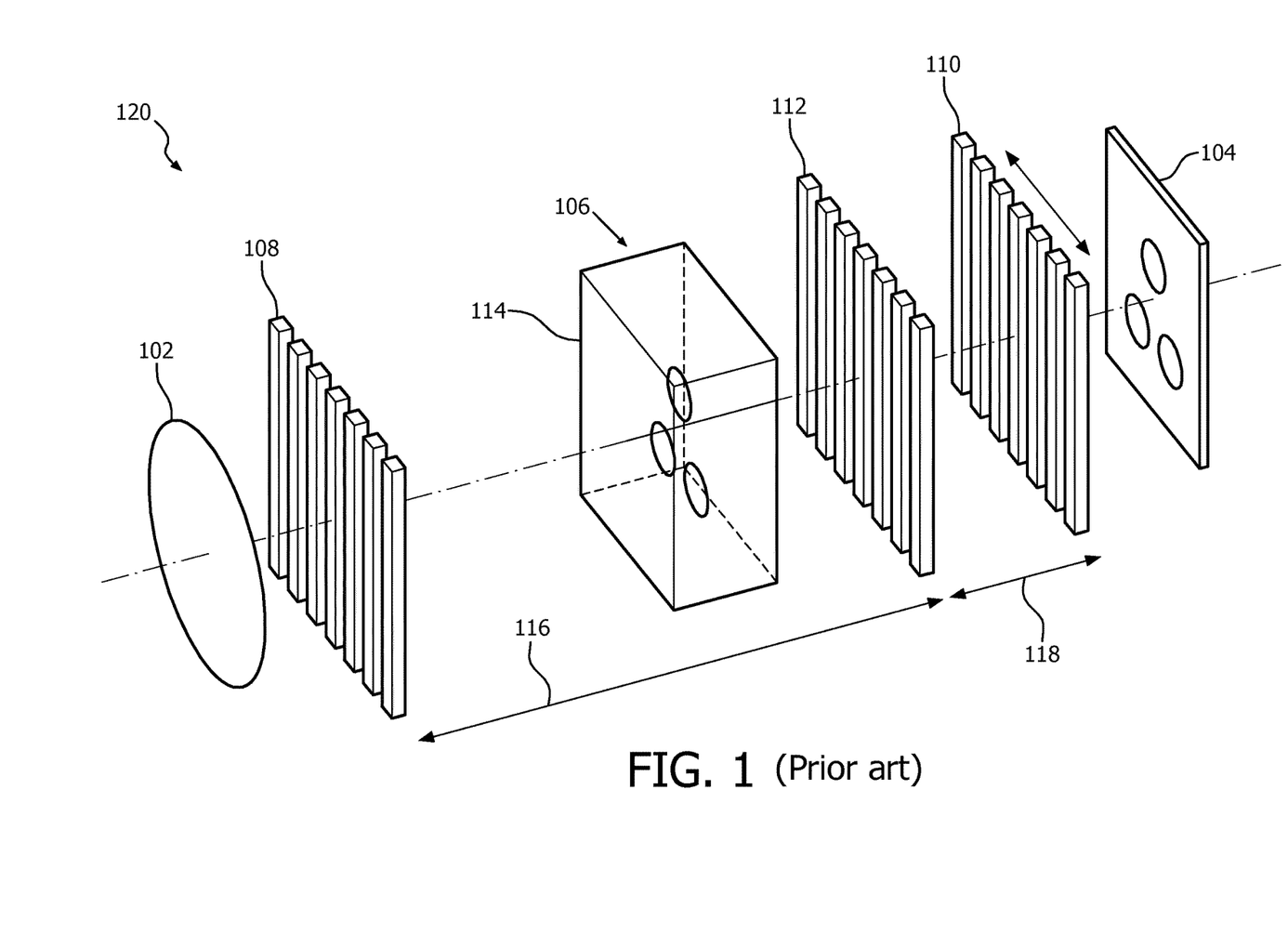
FIG. 1 schematically illustrates a prior art grating-based DPCI apparatus.

Grating-based DPCI overcomes the above-noted limitations. An example grating-based DPCI apparatus is discussed in application Ser. No. 13/514,682, filed Jun. 8, 2012, entitled "Phase Contrast Imaging," and assigned to Koninklijke Philips Electronics N.V., the entirety of which is incorporated herein by reference. The apparatus described in Ser. No. 13/514,682 is shown in FIG. 1. The apparatus includes an X-ray source 102 and a detector 106, which is located opposite the source 102 across an examination region 106. A source grating 108 is located adjacent to the source 102 between the source 102 and the detector 104, an absorber (or analyzer) grating 110 is located adjacent to the detector 104 between the source 102 and the detector 104, and a phase grating 112 is located between an object 114 in the examination region 106 and the absorber grating 110.

The source grating 108 is separated from the phase grating 112 by a distance ("l") 116. The phase grating 112 is separated from the absorber grating 110 by a distance ("d") 118, which corresponds to the Talbot distance ($d=p_1^2/8\lambda$, where $\lambda$ is the wavelength of the incident radiation). The source grating 108, the phase grating 110, and the absorber grating 112 respectively have grating line periods $p_0$, $p_1$ and $p_2$, where $p_2=1/dp_0$, and $p_2=\frac{1}{2}p_1\cdot(d+1)/1$. The source grating 108 creates an array of individually coherent, but mutually incoherent sources. The object 114 in the beam path causes a slight refraction for each coherent subset of X-rays, which is proportional to the local phase gradient of the object. This small angular deviation results in changes of the locally transmitted intensity through the combination of the phase gratings 112 and the absorber grating 114.

The phase grating 110 acts as a beam splitter and divides an incoming X-ray beam essentially into the two first diffraction orders. The diffracted beams interfere and form, in Talbot distances, linear periodic fringe patterns with a periodicity that equals half the phase grating times the geometric magnification factor defined by 1/(1+d). Perturbations of the incident wave front, such as those induced by refraction on the object 114 in the beam, lead to local displacement of the fringes. The absorber grating 110 acts as a transmission mask for the detector 104 and transforms local fringe positions into signal intensity variations. The detected signal profile hence contains quantitative information about the phase shift induced by the object 114. To code and extract the phase information, a phase-stepping approach has been utilized.

US 2009/0092227 A1 discusses a phase stepping approach for grating-based DPCI. With this approach, one of the phase gratings 112 or the absorber grating 110 is translated with respect to the other grating in a transverse direction, which is perpendicular to the lines of gratings in predetermined step sizes over a period of the grating lines. For example, where the absorber grating 110 is translated K discrete steps, each step size will be $p_2/K$, and for each projection, the grating 110 or 112 will step through all K steps. As such, for a scan with L projections, there will be K×L acquisitions, with K acquisitions for each of the L projections. US 2010/0220832 A1 discusses the phase stepping approach in the context of computed tomography with a rotating gantry and grating-based DPCI.

US 2009/0092227 A1 states the phase stepping has to be done with sub-micron accuracy and that the exact parallel orientation of the lines of both gratings may be lost. US 2010/0220832 A1 states that considering the requirements of mechanical accuracy and stability of the order of sub-micron, it is difficult to keep such precision in stepping either grating when the gantry is rotating. US 2009/0092227 A1 then discusses alternative approaches in which neither grating is translated. The alternative approaches include pivoting the phase grating/absorber grating pair or translating the source grating. US 2010/0220832 A1 proposes an alternative in which neither grating is translated. With this approach phase/absorber grating pairs, each with a different and fixed phase offset, is rotated in the beam path from the object to the detector.

With phase stepping, for each discrete measurement the grating 112 or 110 has to accurately step to a discrete position and the measurement taken each integration period, which can be very demanding. By way of example, with a typical integration period on the order of few micro seconds (ms), e.g., IP=100 µs, and K=8, for each measurement, the grating 112 or 110 has to be accurately stepped to position and a measured taken within 12.5 micro seconds. With this example, for each rotation, with one thousand projections each rotation, the grating 112 or 110 has to be accurately stepped eight thousands times in submicron steps, each step within the 12.5 micro seconds. Exasperating the tight mechanical requirements is that the rotating gantry is subject to g force, which causes dynamic structural changes throughout each rotation.

In view of the above, there is an unresolved need for other approaches to grating-based DPCI in which at least one of the gratings is translated.

Aspects described herein address the above-referenced problems and others.

In one aspect, an imaging system is configured for grating-based DPCI. The imaging system includes a rotating gantry that rotates around an examination region, a radiation source, supported by the rotating gantry, that emits radiation that traverses the examination region, a detector array, supported by the rotating gantry, that detects radiation that traverses the examination region, and an interferometer, supported by the rotating gantry, which includes a source grating, a phase grating, and an absorber grating. At least one of the phase grating or the absorber grating continuously translates with respect to the other during an integration period and the detector generates and outputs an electrical signal indicative of the detected radiation, wherein the electrical signal includes an absorption component, a coherence component and a phase component.

In another aspect, a method rotating a gantry supporting a radiation source, an interferometer and a detector array around an examination region, wherein each rotation includes a plurality of integration periods, during an integration period and while rotating the gantry, continuously translating at least one of a phase grating or an absorber grating of the interferometer, with respect to the other, during the integration period and while rotating the gantry, sampling the detector array a predetermined number of times, during the integration period and while rotating the gantry, tracking a position of the translating at least one of the phase grating or the absorber grating, and generating a signal, via the detector array, that includes an absorption component, a coherence component and a phase component.

In another aspect, a method includes continuously translating at least one of a phase grating or an absorber grating during a grating-based DPCI scan, thereby synchronizing phase coding and detection, and generating a detector array output signal that includes an absorption component, a coherence component and a phase component.

The invention may take form in various components and arrangements of components, and in various steps and arrangements of steps. The drawings are only for purposes of illustrating the preferred embodiments and are not to be construed as limiting the invention.

Figure 2:
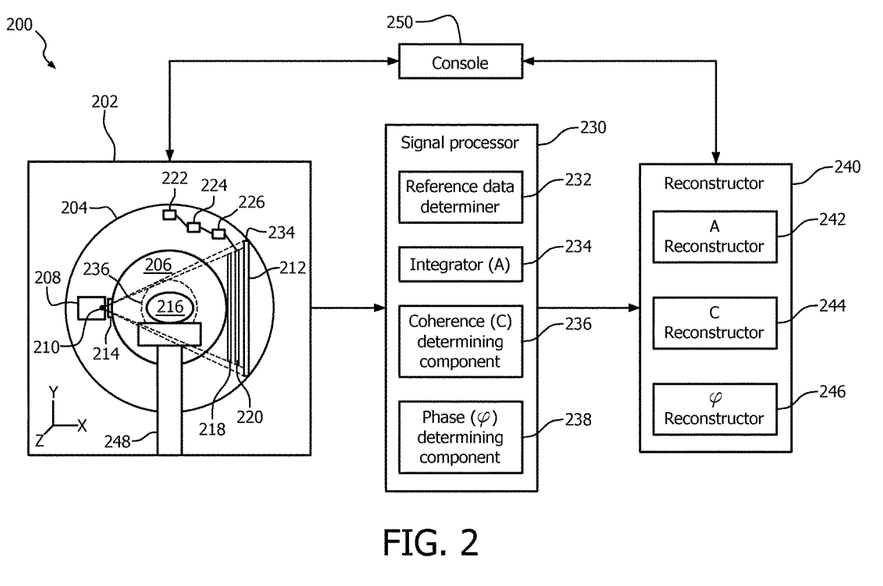
FIG. 2 schematically illustrates an example grating-based DPCI apparatus in which the phase and absorber gratings continuously translate with respect to each other.

FIG. 2 schematically illustrates an imaging system 200, such as a CT scanner, which is configured for grating-based DPCI. The imaging system 200 includes a generally stationary gantry 202, which houses a rotating gantry 204 that is rotatably supported by the stationary gantry 202 and rotates around an examination region 206 about a z-axis. A radiation source 208 (e.g., an X-ray tube) with a focal spot 210 is rotatably supported by the rotating gantry 204, rotates with the rotating gantry 204, and emits radiation that traverse the examination region 206. A radiation sensitive detector array 212 is located opposite the radiation source 208 across the examination region 206. The radiation sensitive detector array 212 detects radiation traversing the examination region 206 and generates a signal indicative thereof.

An X-ray imaging interferometer is also rotatably supported by the rotating gantry 204 and rotates with the rotating gantry 204. The X-ray imaging interferometer includes three grating structures, a source grating 214, a phase grating 218 and an absorber grating 220. The source grating 214, phase grating 218 and absorber grating 220 respectively have grating line periods and are separated by distances, e.g., as discussed in application Ser. No. 13/514, 682, filed Jun. 8, 2012, entitled "Phase Contrast Imaging," and assigned to Koninklijke Philips Electronics N.V., the entirety of which is incorporated herein by reference. Generally, the source grating 214 is adjacent to the focal spot 210 in the path of the radiation, acts as an absorbing mask with transmitting slits, filters the emitted radiation beam, and creates individual coherent (but mutually incoherent) sources, which have sufficient spatial coherence for DPCI.

An object 216 causes slight refraction of coherent x-rays that is proportional to the local gradient of the real part of the refractive index of the object 216, and the angular deviation results in changes of the locally transmitted intensity through the phase grating 218. The phase grating 218 is located adjacent to the object 216 and acts as a beam splitter, dividing an incoming x-ray into diffracted beams that interfere and form linear periodic fringe patterns. The absorber grating 220 acts as a transmission mask for the detector 104 and transforms local fringe positions into signal intensity variations. The phase grating 218 and the absorber grating 220 can be considered a multi-collimator translating the angular deviations into changes of the locally transmitted intensity, which can be detected with a standard or other imaging detector array.

The phase grating 218 and the absorber grating 220 are configured to translate, relative to one another, in a transverse direction, which is perpendicular to the z-axis. This includes translating one or both (in a same direction with different speeds or an opposing direction with the same or different speed) of the phase grating 218 and the absorber grating 220 in the transverse direction. A controller 222 controls a motor 224 which drives a drive system 226 that facilitates translating the grating 218 and/or 220. By way of non-limiting example, in one instance, a support member moveably supports the absorber grating 220. Such movement may be achieved through a bearing or like. For example, a first part of the bearing may be stationarily affixed to the support member and a second part of the bearing may be affixed to the absorber grating 220. In this instance, the second part is free to move (e.g., slide) along the first part under control of the drive system.

In the illustrated embodiment, the controller 222 employs a continuous control algorithm(s) to control the motor 224 and hence translation of the absorber grating 220. With this algorithm, the controller 222 controls the motor 224 to translates the absorber grating 220 at an approximately constant speed. Generally, the speed of the absorber grating 220 phase coding motion will define the sampling. Variations of the speed can be avoided or corrected for in multiple ways. For example the angular gantry position for each sampling interval can be stored and used in the reconstruction to correct for variation. In another embodiment, the phase coding speed can be adaptively controlled relative to a predefined integration interval or by the actual gantry position. In contrast, in a conventional CT scanner, the angular sampling is usually triggered by an angular decoder of the gantry position or by a fixed sampling time.

Figure 2A:
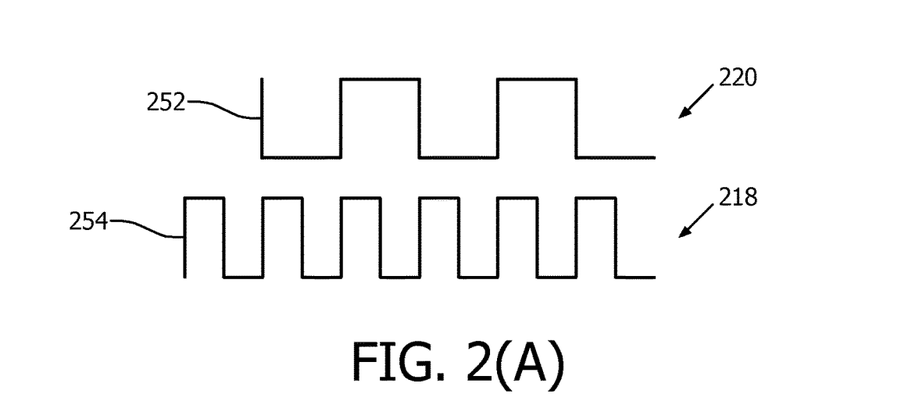
FIGS. 2A, 2B and 2C show the absorber grating continuously translating with respect to the phase grating through a grating line period.
Figure 2B:
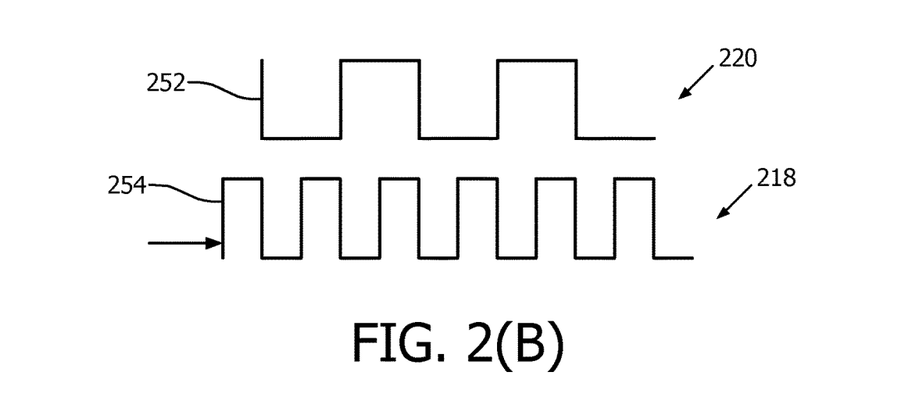
Figure 2C:
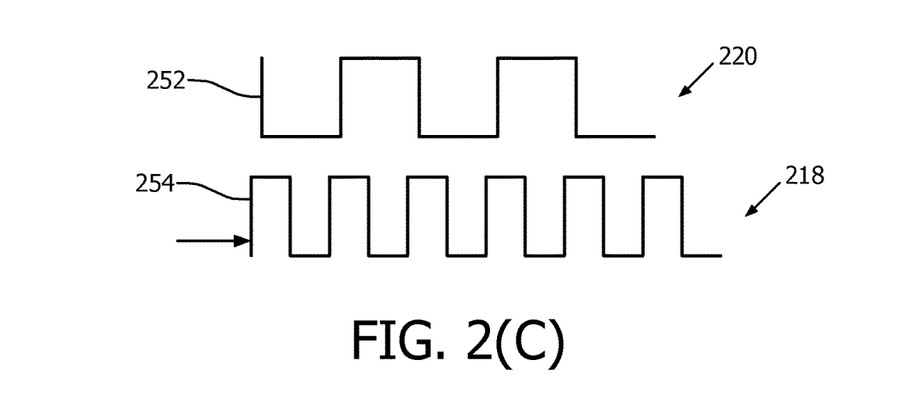

FIGS. 2A, 2B and 2C respectively show the absorber continuously translating through one or more periods of the grating lines 252 and 254 (referred to herein as a phase stepping period) for an integration period. Where the pitch of the grating lines is small enough, a movement of a few millimeters of the grating can cover hundreds of phase stepping periods. For consecutive integration periods, the translating grating(s) can translate in opposing directions and thus oscillate as a function of integration period, or move back to a same starting position for each integration period. In another instance, the translating grating(s) translates in one direction over multiple integration periods before it reverse direction or is moved back to the starting position.

A signal processor 230 process the output of the detector array 212. Generally, an output signal S of the detector array 212 can be expressed as shown in EQUATION 1:

$$S = I_0 A \frac{C\sin(\varphi + 2\pi vt/k + \varphi_0) + 1}{2},$$

where $I_0$ represents a signal intensity without the object 215 in the path of the ray, A represents conventional absorption, C represents a measure of coherence of the incident ray, $\phi$ represents the differential phase, vt represents a relative phase shift between the gratings 218 and 220 (where v represents speed and t represents time), k represents a pitch of the gratings 218 and 220, and $\phi_0$ represents phase without the object 215 in the path of the ray. The output signal S can be considered as including a DC component (A) and a sinusoidal offset with a phase ($\phi$) and amplitude (C).

Figure 3:
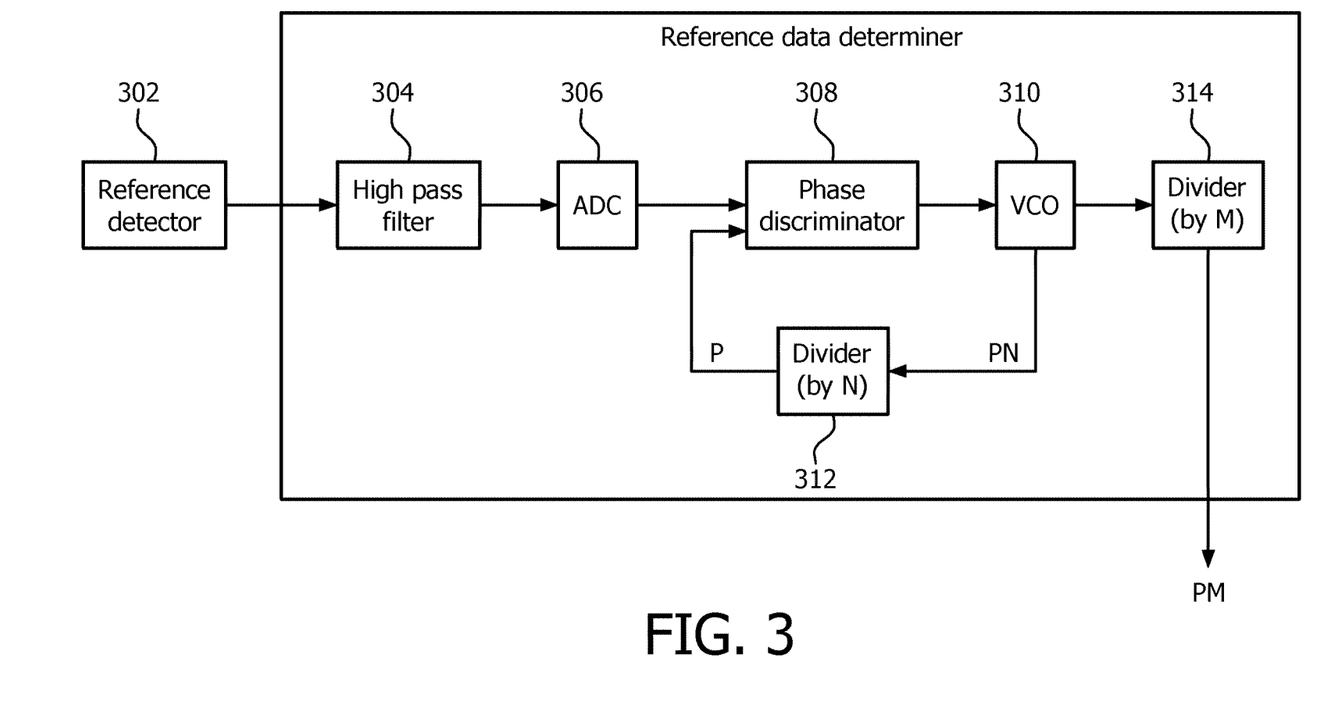
FIG. 3 schematically illustrates an example reference data determiner.

The signal processor 230 includes a reference data determiner 232 that determines at least a signal P indicative of the relative phase between the gratings 218 and 220 and a signal PM, which can be used to define an integration period, based on the signal S from a reference detector. The reference detector can be any detector pixel of the detector array 212. However, the signal output by this pixel may have an unknown phase modulation, if the corresponding incident rays have passed the scanned object 215. In this instance, a correction would be applied. In another instance, a radiation shield is used to block the detector pixel from the incident x-ray beam and an additional (e.g., light) source illuminates the phase grating 218 to generate a proper signal for the phase coding. In the illustrated embodiment, the reference detector is a pixel 234 outside a scan field-of-view 236. The reference detector may include a single pixel or multiple pixels. FIG. 3 schematically illustrates an example reference data determiner 232 and a reference detector 302.

A high pass filter 304 receives an analog signal output by the reference detector 302. The high pass filter 304 filters the analog signal based on a predetermined cut-off frequency. An ADC 306 converts the analog signal into a digital representation of the analog signal, or, a digital signal. A phase discriminator 308 determines a phase of the digital signal. A voltage controlled oscillator VCO 310 generates an output signal PN, which is N times the frequency of P, based on the phase of the digital filtered reference signal, where N defines the resolution of the phase detection and is a positive integer equal to or greater than one. For each phase stepping period (phase coding from 0 to 2 Pi), the signal P has N periods. The phase can be measured by counting the number of periods of signal P until the signal under consideration has a zero-crossing in positive direction. In one instance, this includes counting every number from 0 to N−1. This counted value is indicative of the relative phase (e.g. count=0 means both signal are in phase, count=N/4 means we have a relative phase shift of 90°).

A first divider 312 divides the output of the VCO 310 by N, rendering the signal P, which is indicative of the relative global phase and is fed back to the phase discriminator 308. The phase discriminator 308 compares the phase of the digital filtered reference signal and P and adjusts the frequency of the VCO 310 to keep the two input phases matched. A second divider 314 divides the P by M to determine the integration period PM. M defines how many complete phase stepping periods (0 to 2 Pi) are done for one integration period. In a simple case, M=N means that every phase stepping period represents an integration period. If M=2N, two stepping periods can be integrated to generate a single integration period. Generally, M allows the integration periods to be independent (in integer steps) of the phase stepping speed.

The combination of continuously translating the grating(s) 118 or 120 and the reference detector 302 provides for automatic synchronization of phase coding and detection. This self-synchronization mitigates the higher mechanical accuracy requirements (sub-micron) associated with the phase stepping approach, where, for example, a grating needs to be accurately stepped in submicron discrete increments in submicron time intervals under higher g force while rotating. Thus, unlike the phase stepping approach, the approach described herein is well-suited for rotating interferometers configurations, including high speed rotating gantries since the mechanical accuracy requirements are relaxed.

Returning to FIG. 2, for each pixel of the detector array 212, the signal processor 230 also includes a conventional integrating component 234, a coherence determining component 236, and a phase determining component 238.

The conventional integrating component 234 determines A by integrating the signal S each integration period PM. In one embodiment, the conventional integrating component 234 includes an analog-to-digital (A/D) converter that includes an integrator (e.g., an amplifier and an integrating capacitor) and a comparator, where the A/D converter is a current-to-frequency (I/F) converter. Non-limiting examples of such converters are described in U.S. Pat. No. 6,671,345 B2, filed Nov. 7, 2001, and entitled "Data Acquisition for Computed Tomography," and U.S. Pat. No. 4,052,620, filed Nov. 28, 1975, and entitled "Data Acquisition for Computed Tomography," both of which are incorporated herein by reference in their entirety. Other integrators are also contemplated. The absorption measurement A is only correct if the integration period covers an integer number of phase stepping periods to remove the influence of the phase coding. With rapid changes of the phase of the detector signal, an error can be introduced if the integration period is defined by the signal PM. This error can be corrected with the help of the digital phase discriminator to measure $\phi$. Since the zero-crossing times are measured, the error of unsynchronized integration periods can be estimated and corrected.

The coherence determining component 236 determines C based on S, P, and PM. In one embodiment, the coherence determining component 236 includes an amplitude modulation (AM) demodulator and an analog-to-digital converter. In this instance, the AM demodulator receives the signal S and demodulates the signal S based P. This can be achieved through an envelope detector having a rectifier (anything other component that will pass current in one direction only) and a low-pass filter, or other circuitry. Another example is a product detector that multiplies the incoming signal by the signal of a local oscillator with the same frequency and phase as the carrier of the incoming signal. After filtering the original signal will result.

The phase determining component 238 generates a signal indicative of the phase difference of the detector pixel signal with the phase signal P. This can be done with analog or digital discriminators, and resulting signal represents the phase $\phi$. A simple, robust and powerful digital phase discriminator 238 includes a modulo-N counter connected to the PN signal. Whenever the DC-free detector signal crosses zero, a copy of the actual counter value is stored to indicate the relative phase of the detector signal to the reference signal P. If the related counter values for both transitions (negative to positive and vice versa) are stored, the problem of phase wrapping can be reduced. If M/N>1, the phase discriminator 238 can additionally count the number of full phase stepping periods of the input signal within the frame time. This allows for reduction of the phase wrap problem, in case the phase changes very fast within one frame.

A reconstructor 240 reconstructs the signals generated by the signal processor 240. This includes reconstructing each of A, C, and ϕ, which all contain different information, individually and in combination. Generally, reconstructing A will result in conventional CT image, reconstructing C will result in a dark field image, and reconstructing ϕ will result in phase differential images between neighboring images. In the illustrated embodiment, the reconstructor 240 includes an A reconstructor 240, a C reconstructor 240, and a ϕ reconstructor 240, which respectively reconstruct A, C, and ϕ. In another embodiment, the same reconstructor is used to reconstruct two or more of A, C, and ϕ.

A subject support 248, such as a couch, supports the object 215 in the examination region 206 before, during and/or after scanning a subject or object. A general-purpose computing system or computer serves as an operator console 250. The console 250 includes a human readable output device such as a monitor and an input device such as a keyboard, mouse, etc. Software resident on the console 250 allows the operator to interact with and/or operate the imaging system 100 via a graphical user interface (GUI) or otherwise. This includes selecting a grating-based DPCI imaging protocol, selecting a reconstruction algorithm, initiating scanning, etc.

Figure 4:
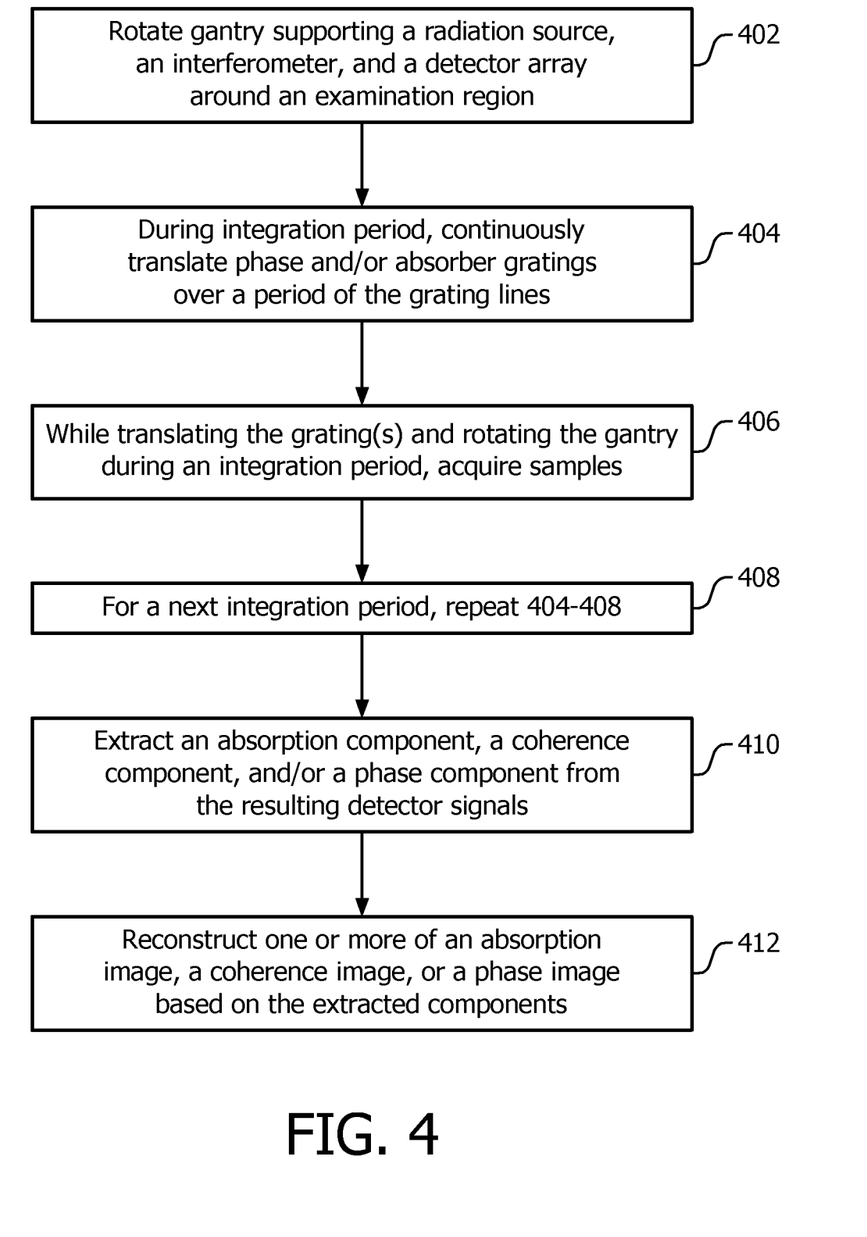
FIG. 4 illustrates an example method for grating-based DPCI in which the phase and absorber gratings continuously translate with respect to each other.

FIG. 4 illustrates an example method for scanning with an imaging system configured for grating-based DPCI.

It is to be appreciated that the ordering of the acts is not limiting. As such, other orderings are contemplated herein. In addition, one or more acts may be omitted and/or one or more additional acts may be included.

At 402, a rotating gantry (supporting a radiation source, an interferometer and a detector array) is rotated about around an examination region.

At 404, during an integration period while rotating the gantry, at least one of the phase grating or the absorber grating continuously translates with respect to the other over one or more periods of the grating lines.

At 406, while continuously translating the grating(s) and rotating the gantry during an integration period, a predetermined number of samples are acquired for a predetermined number of phase stepping periods. Examples of suitable numbers of phase stepping periods per integration period include, but are not limited to, three, four, . . . , eight, . . . twenty, . . .

At 408, for a next integration period, acts 404 to 408 are repeated.

At 410, one or more of an absorption component, a coherence component or a phase component is extracted from the resulting detector signals.

At 412, reconstruct one or more of an absorption image, a coherence image or a phase image based on the extracted absorption, coherence or phase components.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system configured for grating-based DPCI, comprising:
    a rotating gantry rotatable around an examination region;
    a radiation source, supported by the rotating gantry, configured to emit radiation that traverses the examination region;
    a detector array, supported by the rotating gantry, configured to detect radiation that traverses the examination region, where the detector array includes at least one detector pixel which receives radiation unattenuated by a subject or object in the examination region;
    a reference data determiner that at least determines a relative global phase between the phase and absorber gratings based on an output signal of the detector pixel; and
    an interferometer, supported by the rotating gantry, including:
        a source grating,
        a phase grating, and
        an absorber grating,
    wherein the phase grating is configured to continuously translate with respect to the absorber grating during an integration period and the detector is configured to generate and output an electrical signal indicative of the detected radiation, wherein the electrical signal includes an absorption component, a coherence component and a phase component.

2. The imaging system of claim 1, wherein the at least one of the phase grating or the absorber grating is configured to continuously translate with respect to the other during the integration period over one or more grating line periods of the at least one of the phase grating or the absorber grating.

3. The imaging system of claim 2, wherein both the phase grating and the absorber grating are configured to translate, and the phase grating and the absorber grating are configured to translate in opposing directions.

4. The imaging system of claim 2, wherein only the phase grating translates.

5. The imaging system of claim 4, wherein a direction of the phase grating reverses each phase stepping period.

6. The imaging system of claim 4, wherein a direction of the phase grating is the same each phase stepping period.

7. The imaging system of claim 5, wherein an integration period includes multiple phase stepping periods.

8. The imaging system of claim1, where the reference data determiner determines a signal that defines the integration period based on the output signal of the reference pixel.

9. The imaging system of claim 8, further comprising:
    a signal processor that extracts at least one of the absorption component, the coherence component or the phase component from the electrical signal based on the relative global phase and the signal that defines the integration period.

10. The imaging system of claim 9, further comprising:
    a reconstructor that reconstructs the at least one of the extracted component, thereby generating at least one image corresponding to the at least one extracted component.

11. The imaging system of claim 1, further comprising:
    a drive system that translates the at least one of the phase grating or the absorber grating;
    a motor that drives the drive system; and
    a controller that controls the motor,
    wherein the controller employs a continuous control algorithm to control the motor to continuously translate the at least one of the phase grating or the absorber grating.

12. A method, comprising:
rotating a gantry supporting a radiation source, an interferometer and a detector array around an examination region, wherein each rotation includes a plurality of integration periods;
acquiring a reference signal that corresponds to detected radiation traversing the examination region outside of a field of view;
determining a relative global phase between the phase and absorber gratings based on the reference signal;
during an integration period and while rotating the gantry, continuously translating a phase grating of the interferometer, with respect to the stationary absorber grating;
during the integration period and while rotating the gantry, sampling the detector array a predetermined number of times;
during the integration period and while rotating the gantry, tracking a position of the translating phase grating; and
generating a signal, via the detector array, that includes an absorption component, a coherence component and a phase component.

13. The method of claim 12, further comprising:
extracting at least one of the absorption component, the coherence component or the phase component from the signal.

14. The method of claim 12, further comprising:
determining a signal that defines the integration period based on the reference signal.

15. The method of claim 14, wherein the at least one of the absorption component, the coherence component or the phase component are extracted based on the relative global phase and the signal that defines the integration period.

16. The method of claim 13, further comprising:
reconstructing one or more of an absorption image, a coherence image or a phase image based on the extracted at least one of the absorption, coherence or phase components.

17. The method of claim 12, wherein the at least one of the phase grating or the absorber grating continuously translates during each integration period over one or more grating line periods of the at least one of the phase grating or the absorber grating.

18. A method, comprising:
continuously translating at least one of a phase grating or an absorber grating during a grating-based DPCI scan, thereby synchronizing phase coding and detection; and
generating a detector array output signal that includes an absorption component, a coherence component and a phase component;
acquire a reference signal that corresponds to detected radiation traversing the examination region outside of a field of view; and
determine a relative global phase between the phase and absorber gratings based on the reference signal.

* * * * *